(12) United States Patent
Rubie et al.

(10) Patent No.: US 6,712,860 B2
(45) Date of Patent: Mar. 30, 2004

(54) LOWER LEG PROSTHESIS

(75) Inventors: Eric W. Rubie, Salt Lake City, UT (US); Larry J. Hansen, Mesquite, NV (US); Nathan A. Williams, Salt Lake City, UT (US); David J. Wall, Sandy, UT (US)

(73) Assignee: Otto Bock Healthcare LP, Minneapolis, MN (US)

( * ) Notice: Subject to any disclaimer, the term of this patent is extended or adjusted under 35 U.S.C. 154(b) by 65 days.

(21) Appl. No.: 09/781,570

(22) Filed: Feb. 9, 2001

(65) Prior Publication Data

US 2002/0116072 A1 Aug. 22, 2002

(51) Int. Cl.⁷ .................................................. A61F 2/66
(52) U.S. Cl. ........................ 623/55; 623/49; 623/53
(58) Field of Search .............................. 623/53, 54, 55, 623/56, 49

(56) References Cited

U.S. PATENT DOCUMENTS

| | | | |
|---|---|---|---|
| 808,296 A | * 12/1905 | Merrick | |
| 4,547,913 A | 10/1985 | Phillips | 623/27 |
| 4,721,510 A | 1/1988 | Cooper et al. | 623/55 |
| 4,822,363 A | 4/1989 | Phillips | 623/27 |
| 4,892,553 A | * 1/1990 | Prahl | 623/55 |
| 4,959,073 A | 9/1990 | Merlette | 623/55 |
| 5,037,444 A | 8/1991 | Phillips | 623/55 |
| 5,062,859 A | * 11/1991 | Naeder | 623/55 |
| 5,116,384 A | * 5/1992 | Wilson et al. | 623/49 |
| 5,181,932 A | 1/1993 | Phillips | 623/52 |
| 5,181,933 A | 1/1993 | Phillips | 623/55 |
| 5,219,365 A | * 6/1993 | Sabolich | 623/55 |
| 5,258,039 A | * 11/1993 | Goh et al. | 623/55 |
| 5,376,141 A | * 12/1994 | Phillips | 623/55 |
| 5,509,937 A | * 4/1996 | Allard et al. | 623/55 |
| 5,653,767 A | * 8/1997 | Allen et al. | 623/52 |
| 5,701,686 A | 12/1997 | Herr et al. | 36/27 |
| 5,728,177 A | 3/1998 | Phillips | 623/55 |
| 5,800,569 A | 9/1998 | Phillips | 623/53 |
| 5,944,760 A | * 8/1999 | Christensen | 623/55 |
| 6,019,795 A | 2/2000 | Phillips | 623/55 |
| 6,165,228 A | * 12/2000 | Lindh | 623/55 |
| 6,197,066 B1 | * 3/2001 | Gabourie | 623/52 |
| 6,206,934 B1 | * 3/2001 | Phillips | 623/53 |
| 6,280,479 B1 | * 8/2001 | Phillips | 623/52 |

FOREIGN PATENT DOCUMENTS

| | | |
|---|---|---|
| WO | WO 93/04645 | 3/1993 |
| WO | WO 96/04869 | 2/1996 |
| WO | WO 01/01896 | 1/2001 |

OTHER PUBLICATIONS

Phillips, Pub. No. US 2002/0077706 A1, Pub. Date: Jun. 20, 2002, application No. 09/945,092.*

* cited by examiner

*Primary Examiner*—Bruce Snow
*Assistant Examiner*—Cheryl Miller
(74) *Attorney, Agent, or Firm*—Faegre & Benson, LP

(57) ABSTRACT

An improved lower leg prosthesis is disclosed for providing an improved performance, including improved stability and improved multi-axial compliance. The prosthesis includes a two-part lower foot plate, incorporating a forefoot plate and a heel plate, and an upper foot plate that is attached to the forefoot and heel plates by a two-part intermediate elastomeric layer. Forming the lower foot plate and the elastomeric layer each in two parts ensures that the forefoot plate and heel plate function substantially independently of each other, which leads to substantially improved cushioning at heel strike and to improved stability throughout the gait cycle.

27 Claims, 5 Drawing Sheets

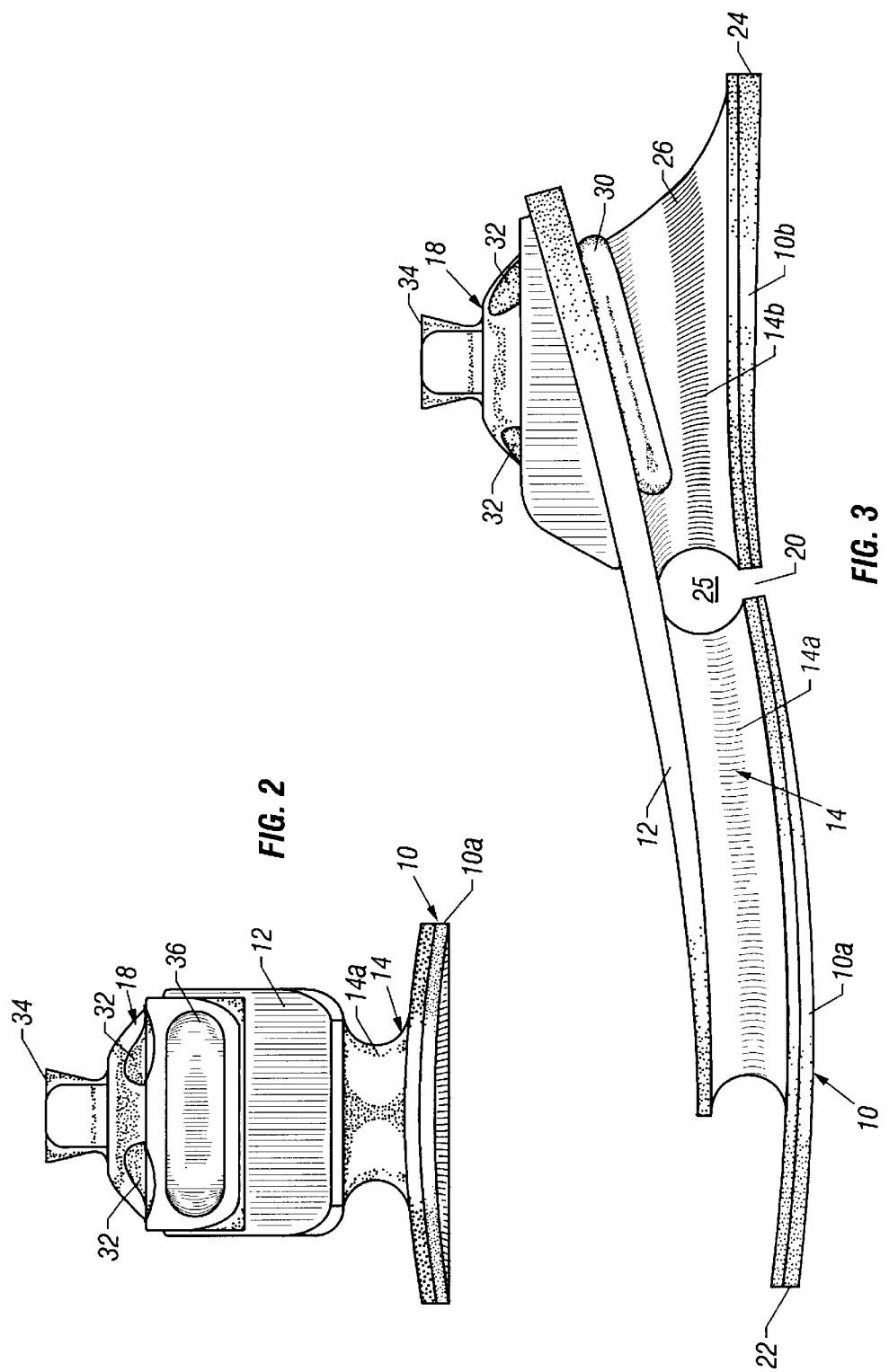

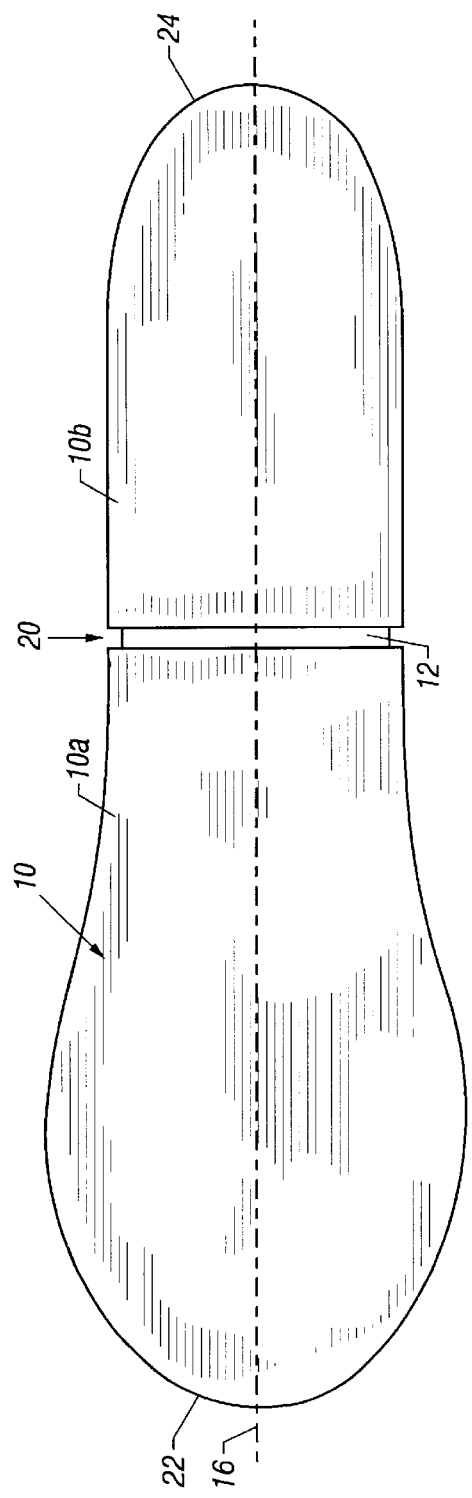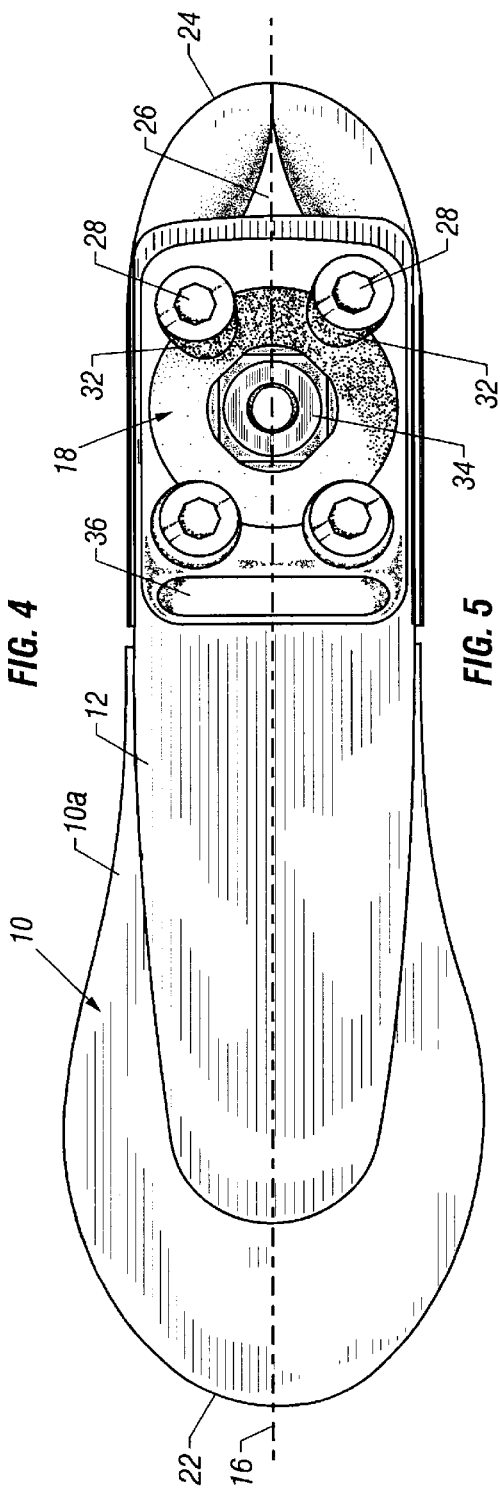

LOWER LEG PROSTHESIS

BACKGROUND OF THE INVENTION

This invention relates generally to lower leg prostheses and, more particularly, to lower leg prostheses configured to duplicate the performance characteristics of the natural human foot and ankle.

Significant advancements in the field of lower leg prostheses have been made in recent years, due largely to the development of composite materials technology. Lower leg prostheses incorporating fiberglass/epoxy and carbon fiber/epoxy composite materials have been developed, which closely duplicate the performance characteristics and feel of the natural human foot and ankle.

One such lower leg prosthesis is sold by CRP, Inc. d/b/a Springlite, under the name Advantage Low Profile. That prosthesis incorporates a flexible lower plate and a relatively rigid upper plate, which are attached together by an intermediate elastomeric layer. A toe portion of the lower plate projects beyond a forward end of the upper plate, and a heel portion of the lower plate projects beyond a rearward end of the upper plate. The lower and upper plates are formed of a high-strength, carbon fiber/epoxy composite material, and the elastomeric layer is formed of a high-density polyurethane material. An attachment pyramid is mounted on the upper plate, for attaching the lower leg prosthesis to a socket for receiving the amputee's residual limb or to an intermediate prosthesis such as a pylon. A crepe sole can be attached to the underside of the lower plate, and a foam foot shell or cosmesis can be placed over the plates, to provide the prosthesis with an appearance of a natural human foot.

The Advantage Low Profile prosthesis described briefly above has enjoyed substantial commercial success. Nevertheless, it is believed that the prosthesis can be improved upon by providing greater stability during use, particularly at heel strike and at toe-off, and also by providing a greater degree of multi-axial movement, thus coming closer to duplicating the performance and feel of the natural human foot and ankle. The present invention fulfills these needs and provides further related advantages.

SUMMARY OF THE INVENTION

The present invention is embodied in an improved lower leg prosthesis that, during use, provides an improved feel at heel strike and that provides improved inversion/eversion compliance. The prosthesis includes an upper foot plate, a forefoot plate, and a heel plate, all aligned along a longitudinal axis. An intermediate elastomeric layer is disposed between the upper and lower plates, for attaching the plates together. This elastomeric layer is configured to allow the forefoot and heel plates to move substantially independently of each other, relative to the upper foot plate.

In more detailed features of the invention, the forefoot and heel plates together have a toe section, a mid-foot section, and a heel section, and those two plates are separated from each other by a gap located in the mid-foot section. The elastomeric layer includes an anterior section disposed between the upper foot plate and the forefoot plate and a posterior section disposed between the upper foot plate and the heel plate, with a gap being defined between the anterior and posterior sections, adjacent to the gap between the forefoot and heel plates. The gap between the forefoot and heel plates preferably has a substantially uniform width, in the range of about 1 to 12 mm. The gap between the anterior and posterior sections of the polyurethane layer preferably has a substantially circular cross-section that blends smoothly with the lower surface of the upper plate and with the upper surfaces of the forefoot and heel plates.

The forefoot plate, heel plate, and upper foot plate all are preferably formed of a composite material incorporating high-strength fibers or filaments, e.g., carbon fiber or fiberglass, and they are configured to be flexible in directions along the longitudinal axis. The forefoot plate can have a thickness that varies along its length, from a maximum at its anterior end to a minimum at its posterior end, and the heel plate likewise can have a thickness that varies along its length, from a minimum at its anterior end to a maximum at its posterior end. The upper foot plate can have a thickness that tapers to a minimum at its anterior end.

The elastomeric layer preferably incorporates a solid, high-density polyurethane. It has a preferred thickness of at least about 2 mm. In the case of applications that do not incorporate a pylon built into the upper foot plate, the elastomeric layer most preferably has a thickness that ranges from about 2 cm adjacent to the forefoot plate, to about 3 cm adjacent to the heel plate. On the other hand, in the case of prostheses that do incorporate a pylon built into the upper foot plate, the elastomeric layer most preferably has a thickness that ranges from about 0.5 cm adjacent to the forefoot plate to about 8 cm adjacent to the heel plate.

In a separate and independent feature of the invention, the forefoot and heel plates together constitute a lower foot plate having a periphery that extends beyond the periphery of the upper plate, and the elastomeric layer extends fully over a substantial portion of that lower foot plate's upper surface, including to a substantial portion of the lower foot plate's periphery. The lower foot plate could, in this feature of the invention, be formed as a single component. The portion of the elastomeric layer portion that extends beyond the upper foot plate's periphery preferably has a uniform thickness of at least about 2 mm.

Other features and advantages of the present invention should become apparent from the following description of the preferred embodiments, taken in conjunction with the exemplary drawings, which illustrate the principles of the invention.

BRIEF DESCRIPTION OF THE DRAWINGS

FIG. 2 is a front elevational view of the foot prosthesis of FIG. 1.

FIG. 3 is a side elevational view of the foot prosthesis of FIG. 1.

FIG. 4 is a bottom plan view of the foot prosthesis of FIG. 1.

FIG. 5 is a top plan view of the foot prosthesis of FIG. 1.

DESCRIPTION OF THE PREFERRED EMBODIMENTS

Figure 1:
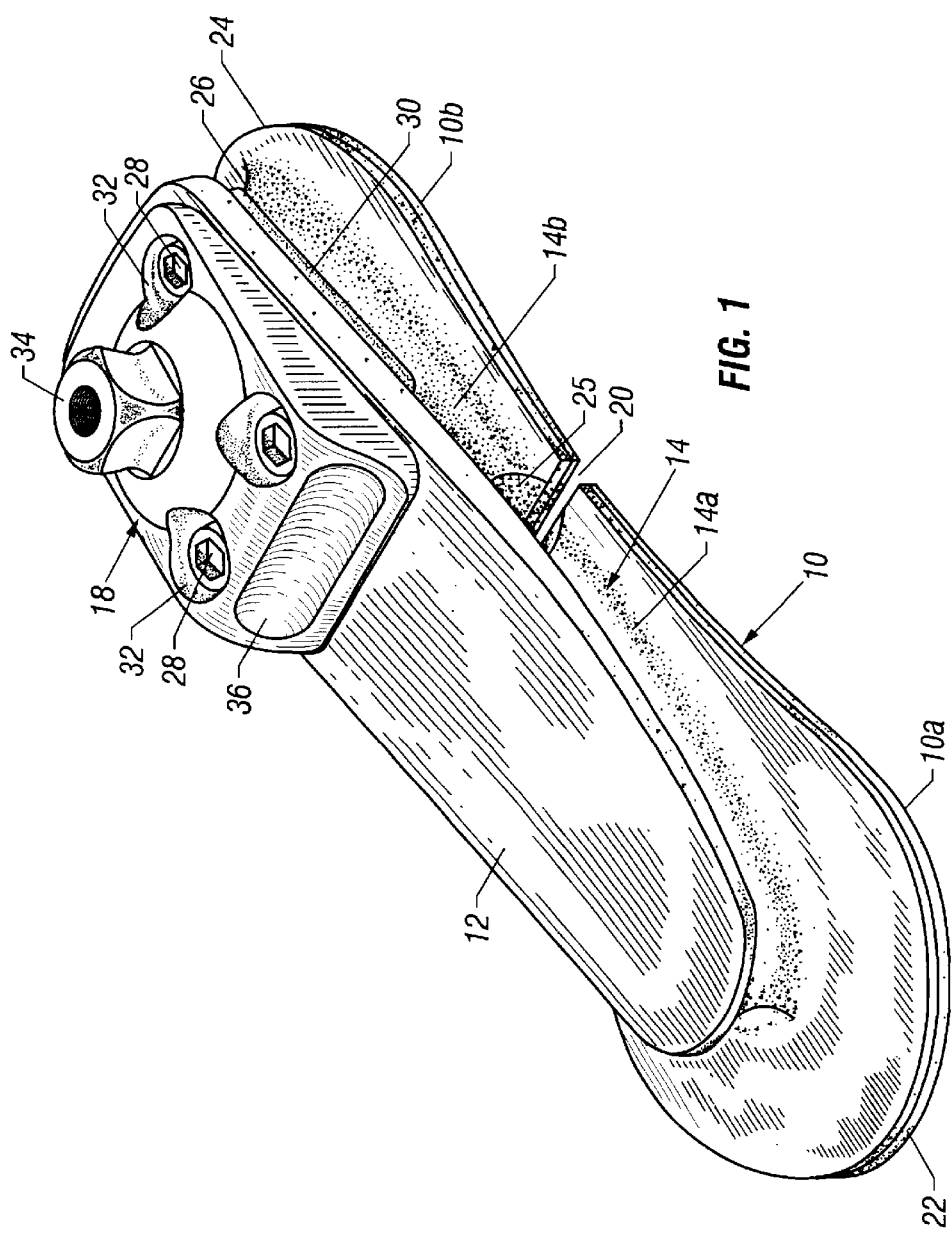
FIG. 1 is a perspective view of a foot prosthesis in accordance with one preferred embodiment of the invention, this prosthesis including a two-part lower foot plate and an upper foot plate that are attached to each other by an intermediate elastomeric layer.

With reference now to the illustrative drawings, and particularly to FIGS. 1–5, there is shown a foot prosthesis in accordance with a first embodiment of the invention. The prosthesis incorporates a two-part lower foot plate 10 and an upper foot plate 12, which are bonded together in spaced relationship by an intermediate elastomeric layer 14. The two-part lower foot plate includes a forefoot plate 10a and a heel plate 10b, which are aligned along a longitudinal axis 16. The intermediate elastomeric layer likewise incorporates two sections aligned along the longitudinal axis, including an anterior section 14a bonding the upper foot plate 12 to the forefoot plate 10a and a posterior section 14b bonding the upper foot plate to the heel plate 10b. An attachment device 18 is secured to the upper surface of the upper foot plate, at its posterior end, for use in attaching the prosthesis to a socket for receiving the amputee's residual limb or to an intermediate prosthesis such as a conventional tubular pylon. A conventional foam cosmesis (not shown) can be placed over the upper and lower foot plates, to provide the prosthesis with the appearance of a natural human foot.

As best shown in FIGS. 1, 3 and 5, the forefoot plate 10a and the heel plate 10b together have a size and peripheral shape that generally match that of a natural human foot, with heel, mid-foot and toe sections. A gap in the form of a slot 20 in the mid-foot section separates the forefoot plate 10a from the heel plate 10b. This slot preferably has a uniform width in the range of 1 to 12 mm, most preferably about 5 mm. Other shapes for the gap alternatively could be used, including shapes that are asymmetric or otherwise non-uniform.

The transverse width of a mid-portion of the forefoot plate 10a preferably is slightly increased in a region corresponding generally to the ball of the natural human foot. The prosthesis of FIGS. 1–5 is configured to be usable for both left and right feet. It will be appreciated, however, that the shapes of the forefoot plate 10a, heel plate 10b, and upper foot plate 12 alternatively could be configured specifically for use as a left foot or as a right foot.

The upper foot plate 12 is sized to be slightly smaller in length and width than the combined forefoot and heel plates 10a and 10b. Specifically, the anterior end of the upper foot plate terminates about 2.5 cm short of the toe tip 22 of the forefoot plate, and the posterior end of the upper foot plate terminates about 2.5 cm short of the heel tip 24 of the heel plate. The anterior end of the upper foot plate is defined by a circular arc that is generally concentric with a circular arc that defines the anterior end of the forefoot plate. Other configurations for the plates alternatively could be used, including configurations in which the forefoot plate and/or the heel plate do not extend beyond the periphery of the upper plate. The upper foot plate also could be configured to include multiple plates, as is preferred for the two-part lower foot plate.

The upper foot plate 12, the forefoot plate 10a, and the heel plate 10b all preferably are formed of a conventional epoxy/carbon fiber composite material. Each preferably has a rectangular cross-section along its entire length. The upper foot plate's thickness is substantially uniform along its posterior half, but tapers to a minimum at its anterior end. The relatively greater thickness of the upper foot plate along its posterior half, together with the presence of the attachment device 18 at that location, render the posterior half of the upper foot plate substantially rigid and inflexible. As described below, however, the anterior half of the upper plate is configured to flex substantially during use of the prosthesis, storing and returning energy in a manner that enhances the prosthesis' performance.

Alternative materials also could be used for the upper foot plate 12, the forefoot plate 10a, and the heel plate 10b, including metals and plastics. If necessary, straps, elastic bands, or other components, can be included, for limiting excessive movement or flexing of the plates in any particular direction. Further, the plates could be made from a material that is substantially inflexible, in which case the desired independent movement between the forefoot plate and heel plate would be provided solely by the elastomeric layer.

The intermediate elastomeric layer 14 preferably is formed of a high-density polyurethane material, although alternative elastomeric materials, including foams, also could be used. As mentioned above, the elastomeric layer's anterior section 14a bonds the upper foot plate 12 to the forefoot plate 10a, and its posterior section 14b bonds the upper foot plate to the heel plate 10b. A non-permanent attachment of the elastomeric layer to the plates alternatively could be used. A gap 25 separates the elastomeric layer's anterior and posterior sections. This gap preferably has a uniform, substantially circular cross-section, which provides excellent durability. It will be appreciated, however, that alternative cross-sectional shapes for the gap, e.g., oval, polygonal or accordion, also could be used. It also will be appreciated that the gap in the elastomeric layer could be eliminated altogether, and the elastomeric layer even could be configured to extend into the gap 20 defined between the forefoot and heel plates.

As best shown in FIGS. 1–3, the elastomeric layer 14 extends over the full height between the upper and lower plates 10 and 12 only in a region located inward of the upper plate's periphery. Outside that region, the elastomeric layer coats the entire upper surfaces of the forefoot and heel plates 10a and 10b, in a uniform thickness in the range of about 2 to 3 mm. Of course, this configuration for the elastomeric layer is only the preferred configuration; the elastomeric layer need not coat the entirety of this outer region, and it need not be of uniform thickness.

As best shown in FIGS. 1–3, the laterally facing sides of the portion of the elastomeric layer 14 that extends over the full height between the upper plate 12 and the forefoot and heel plates 10a and 10b are concave. These sides define a smooth transition to the planar portion adjacent the peripheries of the forefoot and heel plates and a similar smooth transition to the periphery of the upper plate. The anterior section 14a of the elastomeric layer is sized to space the upper foot plate above the forefoot plate by a uniform distance of about 2 cm, and the posterior section 14b is sized to space the upper foot plate above the heel plate 10b by a distance that ranges from about 2 cm adjacent to the slot 20 to about 3 cm at the upper foot plate's posterior end. It will be appreciated that the distance between the upper and lower plates could vary from these values. It also will be appreciated that the laterally facing sides of the elastomeric layer need not be concave; a convex configuration that projects beyond portions of the upper foot plate's periphery alternatively could be used.

The elastomeric layer 14 further defines a wedge section 26 that extends from the underside of the posterior end of the upper foot plate 12 to the tip 24 of the heel plate 10b. This aids in shock absorption at heel strike.

Extending the elastomeric layer 14 over the entire upper surfaces of the forefoot plate 10a and the heel plate 10b more effectively distributes stresses between the plates and the elastomeric layer. The plates thereby can be made slightly thinner, and they can provide increased flexibility and durability.

It will be noted in FIGS. 1 and 3 that the forefoot plate 10a has a thickness profile that varies along its length, being its thickest at the toe tip 22 and thinnest adjacent to the slot 20. Similarly, the heel plate 10b has a thickness profile that varies along its length, being its thickest at the heel tip 24 and thinnest adjacent to the slot. This configuration reduces the stress levels in the portions of the plates adjacent to the slot. It will be appreciated that other thickness profiles alternatively could be used.

The attachment device 18 is secured to the posterior end of the upper foot plate 12 using four screws 28 and a pair of threaded backing strips 30. The screws are seated in individual recesses 32 formed in the attachment device, and the backing strips function to distribute the compressive forces from the screws over enlarged areas. Numerous conventional alternatives to the screws and backing strips also could be used. A pyramid 34 is located on the attachment device's upper side, for use in attaching the prosthesis to a socket for receiving the amputee's residual limb or to an intermediate prosthesis such as a pylon. It will be appreciated that other conventional attachment devices also could be used, including direct bonding or bolting to a socket.

The attachment device 18 is generally wedge shaped, such that its lower surface conforms to the sloping upper surface of the upper foot plate 12 but its upper surface is oriented generally horizontally. The device can be formed of any suitable material, including metals such as stainless steel or titanium, ceramics, composites, and plastics. A weight-reducing cutout 36 can be formed in the device's forward end.

Forming the lower foot plate 10 as separate forefoot and heel plates 10a and 10b, and forming the elastomeric layer 14 as separate anterior and posterior sections 14a and 14b, provides several important advantages. First, this configuration provides the prosthesis with substantially improved stability during use. For example, at heel strike, the anterior end of the heel plate deflects into contact with the ground 38 much sooner than it would if the lower foot plate were formed as a single, unitary plate. Similarly, at toe-off, the posterior end of the forefoot plate remains deflected into contact with the ground for much longer than it would if the lower foot plate were formed as a single, unitary plate. This ensures that a greater surface area on the underside of the prosthesis remains in contact with the ground for a greater time duration during each step, thus significantly improving the prosthesis' stability and correspondingly enhancing the user's sense of security when using the prosthesis.

Figure 6:
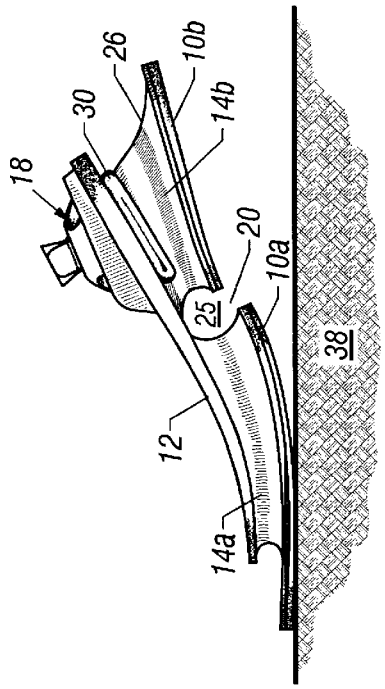
FIGS. 6–9 are a series of side elevational views of the foot prosthesis of FIG. 1, showing the prosthesis in a sequence of stages of a normal step, including full weight on the heel (FIG. 6), mid-stance position (FIG. 7), full weight on the toe (FIG. 8), and toe-off (FIG. 9).

This advantage of increased stability is evident from FIGS. 6–9, which depict the prosthesis at four successive stages of a walking gait. In particular, FIG. 6 depicts the prosthesis at an early stage of the walking gait, where the user has applied substantial weight to the heel plate 10b. At this time, the plate's posterior end has deflected upwardly, to compress the posterior portion of the elastomeric section 14b, while at the same time the plate's forward end has deflected downwardly, to elongate the anterior portion of the elastomeric section. As depicted in FIG. 6, the heel plate's anterior end has deflected fully downwardly into contact with the ground 38. At this time, enhanced plantar flexion stability is achieved even though the prosthesis' forefoot plate 10a has not yet touched the ground. The forefoot plate remains substantially unstressed.

Figure 7:
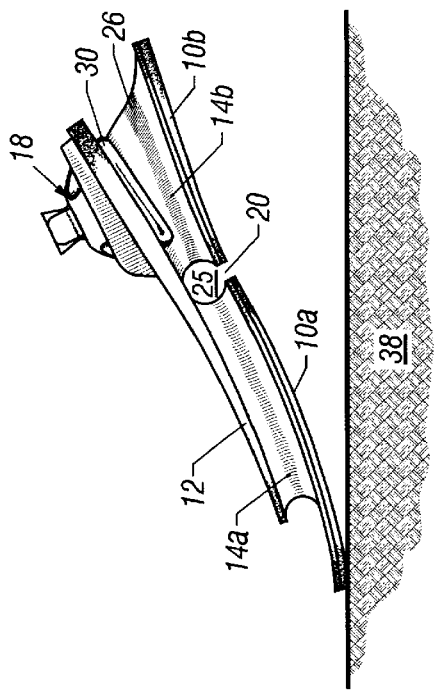

FIG. 7 depicts the prosthesis at a subsequent stage of the walking gait, when a mid-stance condition has been reached.

At this stage, both the anterior section 14a and the posterior section 14b of the elastomeric layer 14 are slightly compressed, but the upper foot plate 12 and the forefoot and heel plates 10a and 10b are substantially unflexed. In the transition from the position of FIG. 6 to the position of FIG. 7, energy stored in the heel plate, as well as energy stored in the posterior section of the elastomeric layer, is recovered and provided to help propel the user forward.

Figure 8:
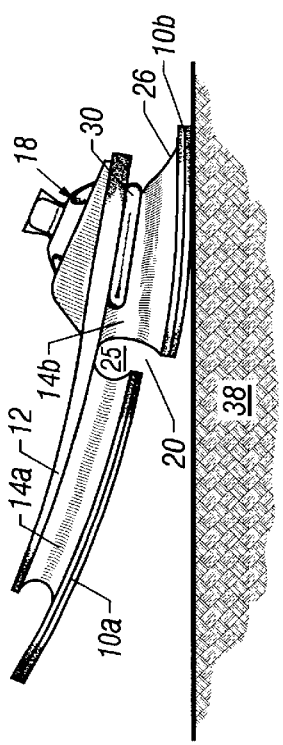

Subsequently, as depicted in FIG. 8, the user's weight has shifted forwardly onto the forefoot plate 10a, and the heel plate 10b has lifted off of the ground 38. At this time, the forefoot plate and the anterior portion of the upper plate 12 are substantially deflected. The anterior portion of the elastomeric section 14a is compressed, and the posterior portion of this elastomeric section is elongated.

Figure 9:
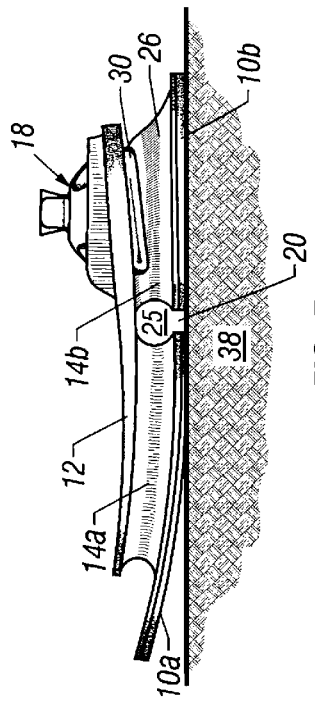

Eventually, as depicted in FIG. 9, the walking gait is completed as the toe tip 22 of the forefoot plate 10a makes final contact with the ground 38. At this time, little weight is being borne by the prosthesis, and the various plates all are substantially unstressed and the elastomeric layer is uncompressed. In the transition from the position of FIG. 8 to the position of FIG. 9, energy stored in the forefoot plate and the upper plate 12, as well as energy stored in the anterior section 14a of the elastomeric layer 14, is recovered and provided to help propel the user forward.

Another performance benefit that results from forming the lower foot plate 10 in two parts, as a forefoot plate 10a and a heel plate 10b, resides in the independent movement of the two parts. This enables the prosthesis to better conform to uneven terrain than a similar prosthesis having a single, unitary lower foot plate.

Yet another performance benefit that results from forming the lower foot plate 10 in two parts resides in reduced resistance to the user's turning about a vertical axis. This reduction is particularly evident when only the heel plate 10b or only the forefoot plate 10a contacts the ground 38, as typically is the case when a turning motion is being made. More particularly, if the user desires to turn left or right as he steps off of the forefoot plate, this turning motion is coupled to the forefoot plate via just the upper plate 12 and the anterior section 14a of the elastomeric layer 14. The posterior section 14b of the elastomeric layer and the heel plate 10b offer no resistance at this time to this turning motion.

Still another performance benefit for the prosthesis is provided by the configuration of the elastomeric layer 14, and in particular by its substantial thickness along its entire length. This thickness facilitates enhanced inversion and eversion movement of the upper plate 12 relative to the forefoot and heel plates 10a and 10b. The prosthesis thereby better duplicates the motion of the natural human foot.

One convenient method for making the prosthesis is to initially form the forefoot plate 10a and the heel plate 10b as a single, unitary plate and to bond that single plate to the upper foot plate 12 using the elastomeric layer 14. After such an assembly has been constructed, the unitary lower plate is cut to form the forefoot plate and the heel plate, separated by the slot 20. This technique ensures that the forefoot and heel plates are properly aligned with each other.

The gap 25 between the anterior and posterior sections 14a and 14b of the elastomeric layer 14 conveniently can be provided at the time the elastomeric layer is formed by placing a dowel in a prescribed position between the upper plate 12 and the two lower plates 10a and 10b before the polyurethane material is poured or otherwise inserted between them. A silicone tool can be used to define the space into which the polyurethane material is inserted. The dowel preferably is sized so that the polyurethane material blends smoothly with the upper and lower plates. The resulting gap in the polyurethane layer has a substantially circular configuration and has a relatively large radius, which together function to enhance the layer's durability.

Sizing the gap 25 to extend fully between the upper plate 12 and lower plate 10 also allows maximum vertical displacement, or elongation, of the elastomeric layer 14 at heel strike and toe-off. This, in turn, provides increased shock absorption at heel strike, as compared to a similar prosthesis having a single, unitary lower foot plate. This increased shock absorption also is evident at less than full loads.

Figure 10:
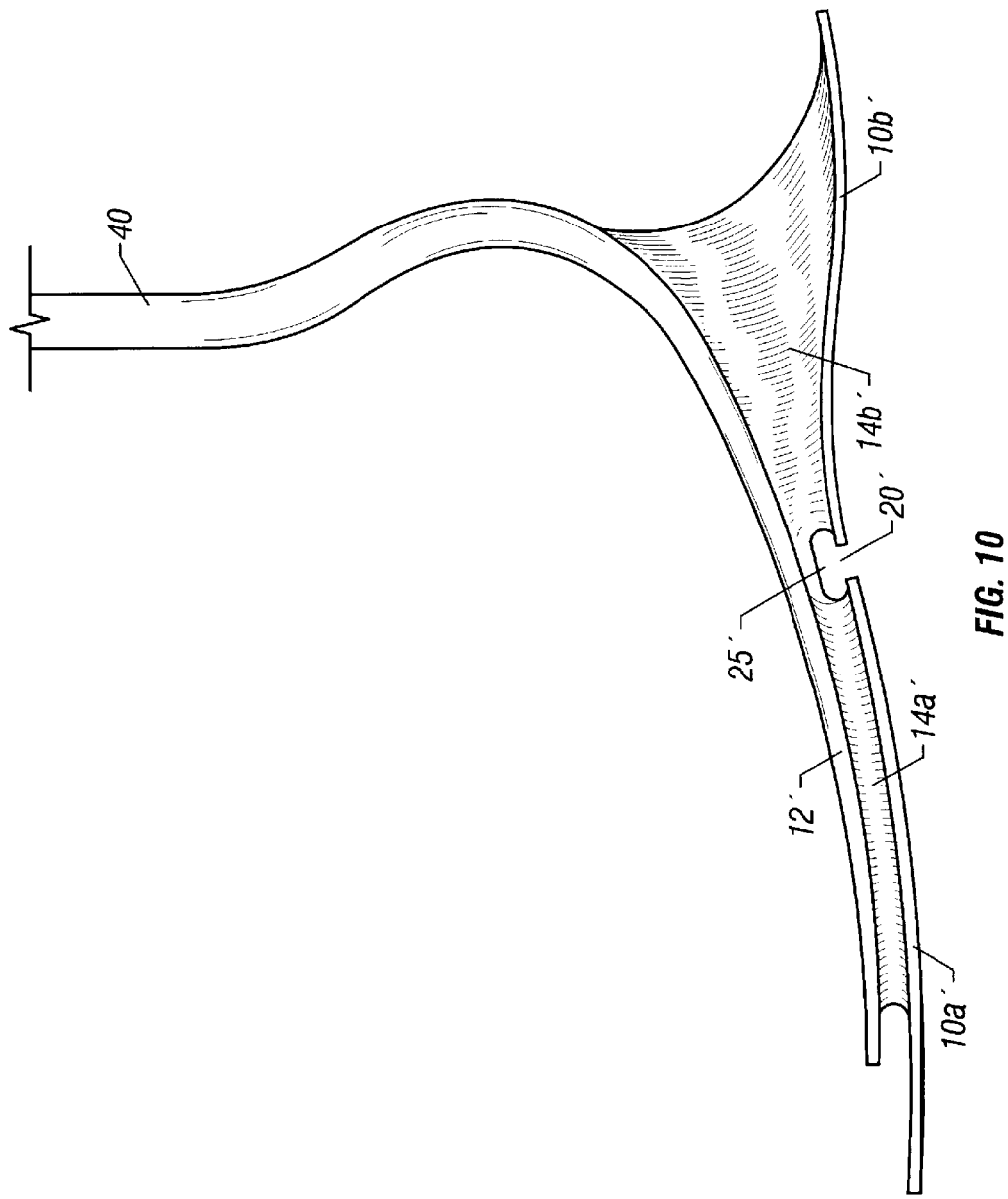
FIG. 10 is a side elevational view of a lower leg prosthesis in accordance with an alternative embodiment of the invention, this prosthesis differing from the prosthesis of FIG. 1 in that its upper foot plate incorporates an integral pylon.

With reference now to FIG. 10, there is shown an alternative embodiment of a lower leg prosthesis in accordance with the invention. Elements of this alternative embodiment that correspond to elements of the embodiment of FIGS. 1–5 are identified by the same reference numerals, but accompanied by asterisks. The alternative embodiment of FIG. 10 differs from the embodiment of FIGS. 1–5 in that it incorporates an upper plate 12' that is integrated with a vertical pylon 40. In this alternative embodiment, the rearward portion of the upper plate curves upwardly to form the pylon. A conventional attachment device (not shown) mounts to the pylon's upper end, for attaching the prosthesis to a socket. Many pylon shapes and configurations could be used in this embodiment.

In other respects, the prosthesis of FIG. 10 is substantially similar to the prosthesis of FIGS. 1–5. It will be noted, however, that the gap 25' between the anterior section 14a' and posterior section 14b' of the elastomeric layer 14 has an oval cross-section, and it does not extend fully up to the lower surface of the upper plate 12'. It also will be noted that the anterior section 14a' has a substantially uniform thickness of about 0.5 cm and that the posterior section 14b' has a thickness that ranges from a minimum of about 0.5 cm, adjacent to the gap 25', to a maximum of about 8 cm.

It should be appreciated from the foregoing description that the present invention provides an improved lower leg prosthesis that, in use, provides an improved performance, including improved stability and improved multi-axial compliance. The prosthesis includes a two-part lower foot plate, incorporating a forefoot plate and a heel plate, and an upper foot plate that is bonded to the forefoot and heel plates by a two-part intermediate elastomeric layer. Forming the lower foot plate and the elastomeric layer each in two parts ensures that the forefoot plate and heel plate function substantially independently of each other, which leads to substantially improved cushioning at heel strike and to improved stability throughout the gait cycle.

Although the invention has been described in detail with reference to the presently preferred embodiments, those of ordinary skill in the art will appreciate that various modifications can be made without departing from the invention. Accordingly, the invention is defined only by the following claims.

We claim:

1. A lower leg prosthesis comprising:
    a forefoot plate and a separate heel plate, located rearward of the forefoot plate and aligned with the forefoot plate along a longitudinal axis, wherein the forefoot and heel plates are separated from each other by a first gap;
    an upper foot plate disposed above the forefoot plate and the heel plate; and
    an intermediate elastomeric layer for attaching the upper foot plate to the forefoot plate and to the heel plate, wherein the elastomeric layer has sufficient thickness and flexibility to allow the forefoot plate and the heel plate to move relative to the upper plate substantially independently of each other, wherein the elastomeric layer comprises an anterior section disposed between the upper plate and the forefoot plate and a posterior section disposed between the upper plate and the heel plate, and wherein a second gap is defined between the anterior and posterior sections, adjacent to the first gap.

2. A lower leg prosthesis as defined in claim 1, wherein:
    the forefoot and heel plates together have a toe section, a mid-foot section, and a heel section; and the first gap is located in the mid-foot section.

3. A lower leg prosthesis as defined in claim 1, wherein the gap that separates the forefoot and heel plates has a substantially uniform width in the range of 1 to 12 mm.

4. A lower leg prosthesis as defined in claim 1, wherein:
    the forefoot and heel plates together have a toe section, a mid-foot section, and a heel section;
    the first gap is located in the mid-foot section.

5. A lower leg prosthesis as defined in claim 4, wherein the first and second gaps both are substantially straight and oriented substantially perpendicular to the longitudinal axis.

6. A lower leg prosthesis as defined in claim 1, wherein the second gap has a substantially circular cross-section.

7. A lower leg prosthesis as defined in claim 1, wherein the second gap blends smoothly with the lower surface of the upper plate and with the upper surfaces of the forefoot and heel plates.

8. A lower leg prosthesis as defined in claim 1, wherein the elastomeric layer has a thickness of at least about 2 mm.

9. A lower leg prosthesis as defined in claim 1, wherein the elastomeric layer incorporates a high-density polyurethane.

10. A lower leg prosthesis as defined in claim 1, wherein the elastomeric layer has a thickness that ranges from a minimum of about 2 cm, adjacent to the forefoot plate, to a maximum of about 3 cm, adjacent to the heel plate.

11. A lower leg prosthesis as defined in claim 1, wherein:
    the upper foot plate is integral with a generally vertically oriented pylon; and the elastomeric layer has a thickness that ranges from a minimum of about 0.5 cm, adjacent to the forefoot plate, to a maximum of about 8 cm, adjacent to the heel plate.

12. A lower leg prosthesis as defined in claim 1, wherein:
    the forefoot plate and the heel plate both are formed of a composite material incorporating high-strength fibers and are flexible in directions along the longitudinal axis;
    the forefoot plate has a thickness that varies along its length, from a maximum at its anterior end to a minimum at its posterior end; and
    the heel plate has a thickness that varies along its length, from a minimum at its anterior end to a maximum at its posterior end.

13. A lower leg prosthesis as defined in claim 1, wherein:
    the forefoot and heel plates together include an outer portion that extends beyond the periphery of the upper plate; and
    the elastomeric layer extends over a substantial part of the outer portion of the forefoot and heel plates, to a substantial portion of the peripheries of the forefoot and heel plates.

14. A lower leg prosthesis as defined in claim 12, wherein the elastomeric layer has a thickness of at least about 2 mm over portions of the elastomeric layer that extend over the outer portion of the forefoot and heel plates.

15. A lower leg prosthesis as defined in claim 1, wherein:
the upper plate is formed of a composite material incorporating high-strength fibers; and
the upper plate has a thickness that tapers from a maximum at the upper plate's posterior end to a minimum at the upper plate's anterior end, such that the upper plate is flexible in directions along the longitudinal axis.

16. A lower leg prosthesis comprising:
a lower foot plate and an upper foot plate disposed in spaced relationship to each other, wherein the lower and upper plates are elongated and are configured to be flexible in directions along a longitudinal axis, wherein the lower foot plate includes an outer portion that extends beyond the periphery of the upper foot plate, the lower foot plate further including a forefoot plate and a heel plate aligned along the longitudinal axis the forefoot and heel plates together have a toe section, a mid-foot section, and a heel section, the forefoot and heel plates being separated from each other by a first gap located in the mid-foot section; and
an intermediate elastomeric layer disposed between, and attaching together, the lower foot plate and the upper foot plate, wherein the elastomeric layer extends over a substantial portion of the upper surface of the outer portion of the lower foot plate, including to a substantial portion of the periphery of the lower plate.

17. A lower leg prosthesis as defined in claim 15, wherein the elastomeric layer extends fully to the periphery of the entire lower foot plate.

18. A lower leg prosthesis as defined in claim 15, wherein the first gap has a substantially uniform width in the range of 1 to 12 mm.

19. A lower leg prosthesis as defined in claim 15, wherein the elastomeric layer comprises an anterior section disposed between the upper plate and the forefoot plate and a posterior section disposed between the upper plate and the heel plate, wherein a second gap is defined between the anterior and posterior sections, adjacent to the first gap.

20. A lower leg prosthesis as defined in claim 19, wherein the second gap has a substantially circular cross-section.

21. A lower leg prosthesis as defined in claim 19, wherein the second gap blends smoothly with the lower surface of the upper plate and with the upper surfaces of the forefoot and heel plates.

22. A lower leg prosthesis as defined in claim 19, wherein the first and second gaps both are substantially straight and oriented substantially perpendicular to the longitudinal axis.

23. A lower leg prosthesis as defined in claim 15, wherein
the forefoot plate and the heel plate both are formed of a composite material incorporating high-strength fibers;
the forefoot plate has a thickness that varies along its length, from a maximum at the forefoot plate's anterior end to a minimum at the forefoot plate's posterior end; and
the heel plate has a thickness that varies along the heel plate's length, from a minimum at the heel plate's anterior end to a maximum at the heel plate's posterior end.

24. A lower leg prosthesis as defined in claim 15, wherein the elastomeric layer incorporates a solid, high-density polyurethane.

25. A lower leg prosthesis as defined in claim 15 wherein the elastomeric layer has a thickness of at least about 2 mm over the outer portion of the lower foot plate.

26. A lower leg prosthesis comprising:
a forefoot plate and a heel plate aligned along a longitudinal axis, wherein the forefoot and heel plates together have a toe section, a mid-foot section, and a heel section, and the forefoot and heel plates are separated from each other by a first gap located in the mid-foot section;
an upper foot plate disposed above the forefoot and heel plates, wherein the upper plate is flexible in directions along the longitudinal axis; and
an intermediate elastomeric layer disposed between the upper foot plate and the forefoot and heel plates, wherein the elastomeric layer includes an anterior section for bonding the upper plate and the forefoot plate and a posterior section for attaching the upper plate and the heel plate, wherein a second gap is defined between the anterior and posterior sections, adjacent to the first gap, wherein the elastomeric layer is configured to allow the forefoot and heel plates to move substantially independently of each other.

27. A lower leg prosthesis comprising:
a forefoot plate and a heel plate aligned along a longitudinal axis, wherein the plates are configured to be flexible in directions along the longitudinal axis, wherein the forefoot and heel plates together have a toe section, a mid-foot section, and a heel section, and the forefoot and heel plates are separated from each other by a first gap located in the mid-foot section;
an upper foot plate disposed above the forefoot and heel plates, wherein the upper plate is flexible in directions along the longitudinal axis; and
an intermediate elastomeric layer disposed between the upper foot plate to the forefoot and heel plates, wherein the elastomeric layer includes an anterior section for bonding the upper plate and the forefoot plate and a posterior section for bonding the upper plate and the heel plate, wherein a second gap is defined between the anterior and posterior sections, adjacent to the first gap/wherein the elastomeric layer has sufficient thickness and flexibility to allow substantial multi-axial movement between the upper plate and the forefoot and heel plates, and wherein the elastomeric layer is configured to allow the forefoot and heel plates to move substantially independently of each other;
wherein the forefoot and heel plates together have a periphery that extends beyond the periphery of the upper plate, and the elastomeric layer extends over substantially the entire upper surfaces of the forefoot and heel plates, including portions of the forefoot and heel plates extending beyond the periphery of the upper plate, in a thickness of at least about 2 mm.

* * * * *